United States Patent
Chan et al.

(10) Patent No.: US 11,087,860 B2
(45) Date of Patent: Aug. 10, 2021

(54) PATTERN DISCOVERY VISUAL ANALYTICS SYSTEM TO ANALYZE CHARACTERISTICS OF CLINICAL DATA AND GENERATE PATIENT COHORTS

(71) Applicant: KONINKLIJKE PHILIPS N.V., Eindhoven (NL)

(72) Inventors: Tak Ming Chan, Shanghai (CN); Choo Chiap Chiau, Shanghai (CN); Niels Roman Rotgans, Eindhoven (NL); Niels Laute, Venlo (NL); Jurriën Carl Gosselink, Lichtenvoorde (NL); Johanna Marie De Bont, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 546 days.

(21) Appl. No.: 15/767,779

(22) PCT Filed: Oct. 19, 2016

(86) PCT No.: PCT/IB2016/056267
§ 371 (c)(1),
(2) Date: Apr. 12, 2018

(87) PCT Pub. No.: WO2017/072628
PCT Pub. Date: May 4, 2017

(65) Prior Publication Data
US 2018/0300454 A1    Oct. 18, 2018

Related U.S. Application Data

(60) Provisional application No. 62/246,675, filed on Oct. 27, 2015.

(30) Foreign Application Priority Data

Dec. 30, 2015    (WO) ................ PCT/CN2015/099836

(51) Int. Cl.
*G16H 50/70*    (2018.01)
*G16H 50/20*    (2018.01)
(Continued)

(52) U.S. Cl.
CPC ............. *G16B 45/00* (2019.02); *G16B 40/00* (2019.02); *G16B 50/00* (2019.02); *G16H 50/20* (2018.01); *G16H 50/70* (2018.01)

(58) Field of Classification Search
CPC ........ G16H 50/20; G16H 50/70; G16H 50/00; G16H 50/10; G16H 50/30; G16H 50/40;
(Continued)

(56) References Cited

U.S. PATENT DOCUMENTS 3,179,839 A    4/1965    Wolfgang
3,297,907 A    1/1967    La Rue et al.
(Continued)

FOREIGN PATENT DOCUMENTS

DE    1491337 A1    6/1969
JP    2007135683 A    6/2007
(Continued)

OTHER PUBLICATIONS

Wongsuphasawat, Krist, and David Gotz. "Exploring flow, factors, and outcomes of temporal event sequences with the outflow visualization." IEEE Transactions on Visualization and Computer Graphics 18.12 (2012): 2659-2668. (Year: 2012).*
(Continued)

*Primary Examiner* — Jesse P Frumkin

(57) ABSTRACT

In pattern discovery visual analytics, a patient data table (14) is generated that tabulates, for each patient, attribute values for a set of attributes. A positive or negative prediction is generated for each patient for a target value of a target attribute using a prediction pattern (20) of attribute values for w attributes (22). The prediction is positive if at least a
(Continued)

threshold fraction (26) of the w attributes of the patient match the prediction pattern, is negative otherwise. Patients are grouped into a selected proportion of a confusion matrix (30) in accord with the positive or negative predictions and actual values of the target attribute T in the patient data table. A display component (4) displays a representation (42) of patient statistics for the selected proportion of the confusion matrix on a per-attribute basis for attributes of the w attributes. A patient cohort (44) is identified using the representation.

15 Claims, 5 Drawing Sheets

(51) Int. Cl.
   *G16B 45/00* (2019.01)
   *G16B 40/00* (2019.01)
   *G16B 50/00* (2019.01)

(58) Field of Classification Search
   CPC ........ G16H 50/50; G16H 50/60; G16H 50/80; G16B 45/00; G16B 40/00; G16B 50/00; G16B 99/00; G16B 40/10; G16B 40/20; G16B 40/30; G16B 50/10; G16B 50/50; G16B 50/20; G16B 50/40; G16B 50/70; G06F 19/30; G06F 19/32; G06F 19/34; G06Q 50/22; G06Q 50/24
   See application file for complete search history.

(56) References Cited

U.S. PATENT DOCUMENTS

| | | |
|---|---|---|
| 3,368,104 A | 2/1968 | McCullough |
| 3,450,930 A | 6/1969 | Lien |
| 3,453,483 A | 7/1969 | Leidigh |
| 3,644,778 A | 4/1972 | Kohn |
| 3,700,963 A | 10/1972 | Shimada |
| 3,902,098 A | 8/1975 | Tanaka et al. |
| 3,936,695 A | 2/1976 | Schmidt |
| 3,940,655 A | 2/1976 | Palluel et al. |
| 3,987,332 A | 10/1976 | Convery |
| 3,995,193 A | 11/1976 | Horigome et al. |
| 4,207,494 A | 6/1980 | Hatakenaka et al. |
| 6,604,115 B1 | 8/2003 | Gary et al. |
| 2009/0027040 A1 | 1/2009 | Docherty et al. |
| 2013/0073311 A1 | 3/2013 | Lynn et al. |
| 2013/0103719 A1* | 4/2013 | Gotz ............ G06T 11/206 707/798 |
| 2013/0144679 A1 | 6/2013 | Burnett et al. |
| 2014/0108380 A1* | 4/2014 | Gotz ............ G06F 16/904 707/722 |
| 2014/0222719 A1* | 8/2014 | Poulin ........... G06F 19/00 706/11 |
| 2014/0257045 A1* | 9/2014 | Hu ............... G16H 50/70 600/300 |
| 2015/0006456 A1 | 1/2015 | Sugharsan |
| 2015/0097977 A1 | 4/2015 | Watanabe |

FOREIGN PATENT DOCUMENTS

| | | |
|---|---|---|
| JP | 2011203976 A | 10/2011 |
| JP | 2012256178 A | 12/2012 |
| WO | 2007117141 A1 | 10/2007 |
| WO | 2012029931 A1 | 3/2012 |
| WO | 2013142268 A1 | 9/2013 |

OTHER PUBLICATIONS

Krause, Josua, Adam Perer, and Harry Stavropoulos. "Supporting iterative cohort construction with visual temporal queries." IEEE transactions on visualization and computer graphics 22.1 (2015): 91-100. (Year: 2015).*

Huang, Chih-Wei, et al. "A richly interactive exploratory data analysis and visualization tool using electronic medical records." BMC medical informatics and decision making 15.1 (2015): 1-14. (Year: 2015).*

IEEE Transactions on Electron Devices, vol. ED-24, No. 1, Jan. 1977, pp. 3-12 by Takao Kagryarna, Yoshihiro Morizurni, Eiichi Watanabe.

Wongsuphasawat, K., et al., "Outflow: Visualizing Patient Flow by Symptoms and Outcome", (2011). https://www.slideshare.net/kristw/outflow-visualizing-patients-flow-by-symptoms-outcome.

Gotz, D. et al., "A methodology for interactive mining and visual analysis of clinical event patterns using electronic health record data", Journal of Biomedical Informatics, vol. 48, Apr. 1, 2014, Abstract.

http://www.sas.com/en_in/home.html.

* cited by examiner

PATTERN DISCOVERY VISUAL ANALYTICS SYSTEM TO ANALYZE CHARACTERISTICS OF CLINICAL DATA AND GENERATE PATIENT COHORTS

CROSS-REFERENCE TO PRIOR APPLICATIONS

This application is the U.S. National Phase application under 35 U.S.C. § 371 of International Application No. PCT/M2016/056267, filed on Oct. 19, 2016, which claims the benefit of U.S. patent application Ser. No. 62/246,675, filed on Oct. 27, 2015 and PCT/CN2015/099836 filed on Dec. 30, 2015. These applications are hereby incorporated by reference herein.

FIELD

The following relates generally to the medical arts, oncology arts, clinical trial design arts, clinical diagnostic and monitoring arts, and related arts.

BACKGROUND

A wide range of medical information systems are employed in the healthcare industry, ranging from general-purpose electronic health record (EHR) systems or electronic medical record (EMR) systems, to more specialized information systems such as cardiovascular information system (CVIS) deployments. These information systems store diverse patient information in a wide range of formats. The information may include, for example: demographic data such a gender (having values of "male" or "female"), ethnicity (having various designations), and age in years; vital sign readings such as heart rate in beats/minute, respiration in breaths/minute, blood pressure in mmHg, $SpO_2$ percentage values; blood test results in units such as millimoles/liter, milligrams/liter, or so forth; genomic data; quantitative imaging data in units of length, density, time, or other units; and so forth. The information in a medical information system may be leveraged for various purposes, such as identifying potential subjects for a clinical trial or other medical study, or identifying patients similar to a current patient undergoing clinical treatment for comparative analysis. Such a group of patients with defined similarities is commonly referred to as a patient cohort, and appropriate selection of a patient cohort is an important part of designing a clinical trial, or performing probative comparisons with a current clinical patient.

However, existing medical information systems are difficult to navigate for the purpose of identifying appropriate cohorts. Medical information systems are usually constructed for different purposes, typically for recording and retaining individual patient records. The information is indexed by patient, and is usually retrieved on a per-patient basis. For example, a patient's doctor may retrieve patient medical information for clinical purposes, or a hospital administrative agent may retrieve patient information for purposes of hospital room assignment, medical insurance billing, or so forth. Such retrieval operations are for a particular patient, and for this purpose it is feasible for the doctor or administrative agent to manually "wade through" the relatively haphazardly organized patient information of the single patient's medical record.

On the other hand, leveraging such a medical information system for generating patient cohorts requires very different analyses. In this case, many hundreds, thousands, or more patients may need to be analyzed to identify a meaningful cohort. In many cases, the patient information relevant for defining a cohort may not be readily apparent. Still further, for tasks such as designing a clinical trial the patients selected for the cohort may have incomplete medical information due to their treatment being "in progress". For example, oncology patients eligible for participation in a clinical trial to study a new cancer treatment must be in a relatively early stage of the cancer treatment, since patients who have been cured, or who are undergoing or have undergone treatment by an alternative therapy that is incompatible with the clinical trial, or patients who have deceased, cannot participate. This means the patient cohort for the trial may need to be identified by patient information that is available at an early stage of cancer treatment. This limits the amount of information available for selecting the patient cohort for the clinical trial. Similar issues arise in selecting a patient cohort for comparison with a current clinical patient who is currently in an early stage of treatment.

The following discloses new and improved systems and methods that address the above referenced issues, and others.

SUMMARY

In one disclosed aspect, a pattern discovery visual analytics device comprises: a patient information database and a computer including a display component. The computer is programmed to perform a method including: generating a patient data table from patient information contained in the patient information database that tabulates, for each patient of the patient data table, attribute values for a set of attributes; for each patient of the patient data table, generating a positive or negative prediction for a target value t of a target attribute T of the set of attributes using a prediction pattern of attribute values for w attributes of the set of attributes, the prediction for a patient being a positive prediction if at least a threshold fraction e of the w attributes of the patient in the patient data table match the prediction pattern and being a negative prediction otherwise; grouping patients of the patient data table into at least a selected proportion of a confusion matrix that includes true positive, false positive, true negative, and false negative proportions in accord with the positive or negative predictions for the target value t of the target attribute T and actual values of the target attribute T in the patient data table; and displaying, on the display component of the computer, a representation of patient statistics for the selected proportion of the confusion matrix on a per attribute basis for attributes of the w attributes.

In another disclosed aspect, a computer-implemented pattern discovery visual analytics method comprises: for each patient of a population, generating a positive or negative prediction for a target value t of a target attribute T using a computer that is programmed to compare a prediction pattern for w attributes to corresponding attribute values of the patient; using the computer, grouping patients of the population into at least a selected proportion of a confusion matrix that includes true positive, false positive, true negative, and false negative proportions in accord with the positive or negative predictions for the target value t of the target attribute T and actual values of the target attribute T for the patients; and displaying, on the display component of the computer, a representation of statistics for the selected proportion of the confusion matrix with attributes of the w attributes represented by attribute value nodes each representing the fraction of patients of the selected proportion having the corresponding attribute value.

In another disclosed aspect, a non-transitory storage medium stores instructions executable by a computer having a display component to perform a pattern discovery visual analytics method comprising: for each patient of a population, generating a positive or negative prediction for a target value t of a target attribute T by applying a model parameterized by w attributes to attribute values of the patient for the w attributes; grouping patients of the population into at least a selected proportion of a confusion matrix that includes true positive, false positive, true negative, and false negative proportions in accord with the positive or negative predictions for the target value t of the target attribute T and actual values of the target attribute T for the patients; and displaying, on the display component of the computer, at least a portion of a directed graph of the w attributes. In the directed graph, the w attributes are ordered in a defined sequence, each attribute is represented by attribute value nodes representing attribute values assumed by the attribute for the patients, and edges of the directed graph comprise flow connectors each extending between two adjacent attributes in the defined sequence and connecting an attribute value node of one of the adjacent attributes with an attribute value node of the other of the adjacent attributes.

One advantage resides in providing visual information on patient attributes that contribute to a predictive pattern for predicting patient outcome or for predicting another late-stage patient attribute.

Another advantage resides in providing visual information on patient attributes in the larger context of a time sequence of clinical stages in which different patient attribute values are generated (i.e. become available) at various different clinical stages.

Another advantage resides in providing a user interface to facilitate selection of patient cohorts from patients of a medical information system.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Pattern discovery visual analytics techniques disclosed herein leverage recognition that in a clinical process (or any other stage-based process), information of an individual patient (a sample) is obtained progressively in a time manner. For example, the percutaneous coronary intervention (PCI) procedure in cardiology progressively generates more patient information according to time oriented stages starting from historical and demographic information collected during patient admission, test results generated by pre-procedure laboratory test, followed by in-procedure measurements of lesions and devices, still later followed by post-procedure laboratory test results, discharge statuses and medications, or so forth. Identifying patient groups (cohorts) satisfying certain time-constrained criteria according to a chosen prediction target is meaningful for early intervention for high risk patients to improve quality of care. Such patient cohort selection also has value for clinical research, for example to choose patients to enroll in a clinical trial.

Figure 1:
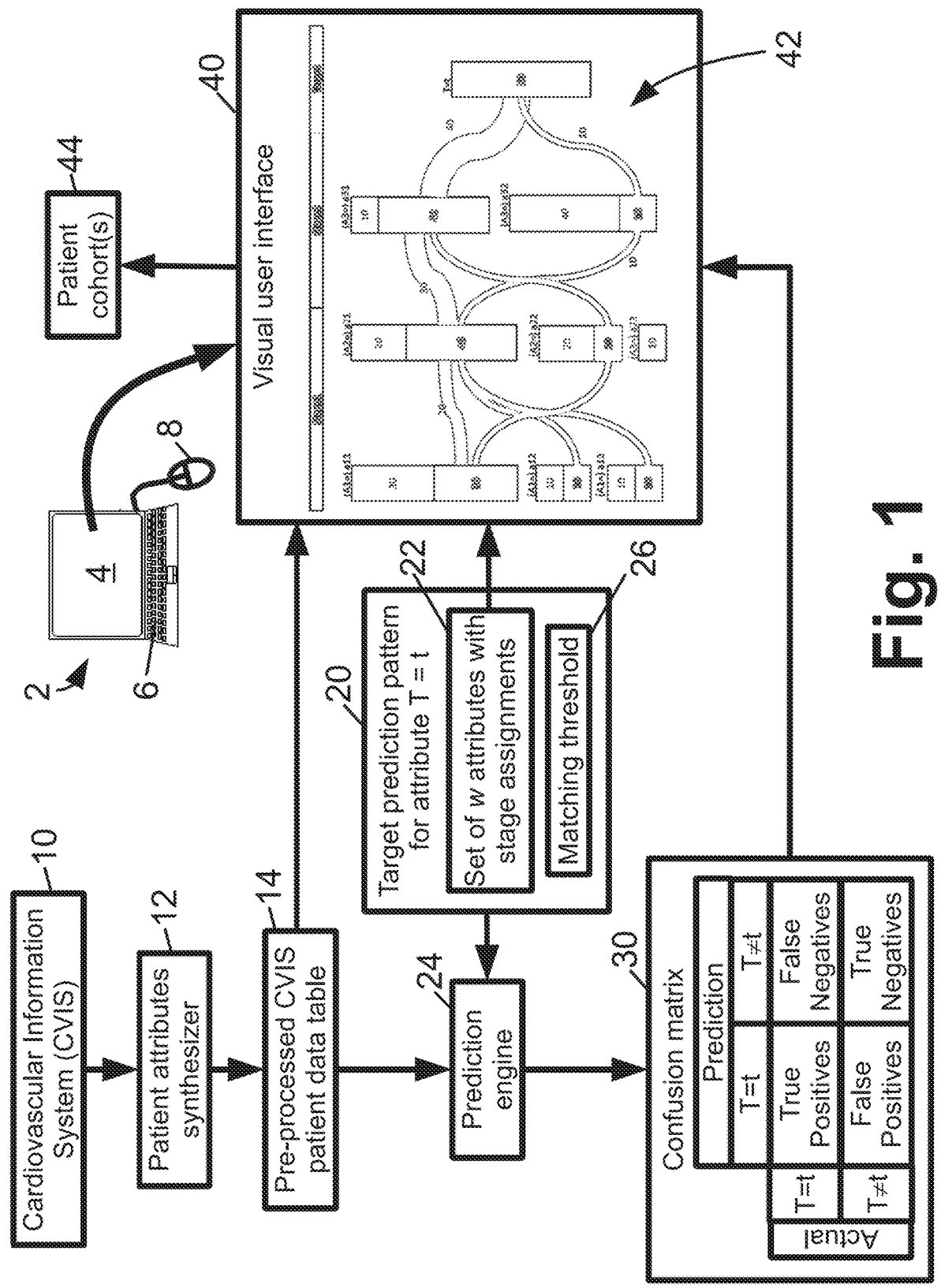
FIG. 1 diagrammatically shows an illustrative pattern discovery analytics device for analyzing characteristics of clinical data and generating patient cohorts.

With reference to FIG. 1, an illustrative pattern discovery visual analytics device comprises a computer 2 that includes a display component 4 and at least one user input device 6, 8. The display component 4 may, for example, be an LED display device, an LCD display device, or so forth, and in some embodiments may comprise two (or even more) such display devices. The illustrative user input devices include a keyboard 6 and a mouse 8, but additional or other user input devices are contemplated, such as a trackball, trackpad, tough-sensitive display (integral with the display component 4), or so forth. The illustrative device is a unitary device such as a desktop computer or notebook computer in which the electronic processor (not shown) of the computer 2 is integral with or in close proximity to the display component 4 and user input device(s) 6, 8. In other embodiments, the electronic processor may be located remotely—for example, the computer may be a server computer connected with the user interfacing components 4, 6, 8 via the Internet and/or a wide area network (WAN), local area network (LAN), or so forth.

In an illustrative example herein, a Cardiovascular Information System (CVIS) 10 is considered as an illustrative patient information database. More generally, however, the disclosed pattern discovery visual analytics techniques can be employed in conjunction with substantially any type of patient information database, such as by way of further illustration an electronic health record (EHR) system or an electronic medical record (EMR) system. In typical patient records stored in CVIS 10, such information is usually stored in large quantities due to the large number of cardio-vascular disease patients whose records are stored in the CVIS 10. Such information is also usually stored in a wide range of different raw formats, with a wide range of different quantifications or units. A physician, clinical trial designer, or the like faces a difficult or impossible task in filtering through this information to retrieve patient cohorts according to meaningful factors. In many cases, those meaningful factors are not known in advance, or are buried among hundreds of other attributes, or may not (yet) be available for patients in early stages of treatment.

Pattern discovery visual analytic techniques disclosed herein leverage models parameterized by a set of (without loss of generality) w attributes, typically in the form of predictive patterns of values for the w attributes, and optionally further leverage a known time sequence of clinical stages for a given type of clinical treatment to order various patient attributes in a defined sequence. In this approach, each patient attribute is assigned to a clinical stage at which the attribute value is typically generated. Thus, the defined sequence of patient attributes corresponds, at least approximately, to the time order in which values of the attributes are generated. These "patient flows" facilitate detection of sub-groups of patients of interest, that is, patient cohort identification. The pattern discovery visual analytic techniques disclosed herein leverage such a patient flow in cohort generation and analytics using a data-driven and model-driven (e.g. pattern-driven) approach. Visual analytics enable effective discovery and retrieval of patients according to certain sub-patterns in a time-oriented clinical flow, thus significantly increasing the efficiency of generating usable cohorts for clinical research and patient follow-up schemes to improve quality of care.

The disclosed pattern discovery visual analytic techniques employ a pattern based generation method to arrange patient data into different time-oriented stages and cohorts (matching/mismatching combination groups) that enables users to select and retrieve any of these groups conveniently. A time (stage) and pattern organization method with visual and interactive elements enables users to identify the meaningful characteristics of patient sub-groups effectively and efficiently, including but not limited to their matching/mismatching to the pattern, distributions against other data, and/or time-oriented stage arrangements.

With continuing reference to FIG. 1, patient information stored in the CVIS 10 is pre-processed by a patient attributes synthesizer 12 to generate a patient data table 14 (which may be physically organized as multiple tables or other suitable data structures, e.g. in a relational database) that consists of categorical/nominal values. The patient data table 14 tabulates, for each patient of the patient data table 14, attribute values for a set of attributes. An attribute is a measurable property applicable individual patients, and each attribute is suitably stored in one column in the patient data table 14, with each row representing one patient (or one patient record). Depending upon the chosen data structure, these table rows and columns may be swapped, or the patient data table 14 may have some other suitable data structure such as a relational database. Table 1 illustrates a suitable patient data table format. In this illustrative example, "ID" represents the patient identifier, and the remainder of the header row identifies various attributes: "Gender", "PCI History", "Hemoglobin", "MI History" (denoting myocardial infarction history), "CRP" (denoting the C-reactive protein laboratory test), and "Bleeding". Each attribute can assume a value within some set of allowable attribute values for the attribute. For example, the "Gender" attribute can assume values in the set {Male, Female}. In some embodiments, the patient attributes synthesizer 12 converts some or all of the patient attributes to binary attributes for which the set of allowable attribute values has exactly two allowable values. For example, in the case of numerical values of clinical test results, such a conversion can convert the test values to either "Normal" or "Abnormal" based on clinical guidelines for the laboratory test (which may take into account factors such as patient age, weight, gender, chronic conditions, or so forth). Such conversion advantageously facilitates simplified and more clinically meaningful predictive pattern matching; however, attributes with more than two possible values, or with continuous values such as being in the range (0,5) or (0,100%) are also contemplated. It will be appreciated that not all information contained in the CVIS 10 may be incorporated into the patient data table 14, and moreover some patients may have no attribute value for certain attributes (e.g., if the corresponding laboratory test has not been performed for that patient). Similarly, some patients of the CVIS 10 may be omitted from the patient data table 14; for example, if the purpose of the pattern discovery visual analysis is to generate a patient cohort for a pregnancy study, then only female patients of the CVIS 10 may be included in the patient data table 14. The attributes whose values are tabulated in patient data table 14 define a set of attributes upon which the pattern discovery visual analytic device can operate. It should be appreciated that although illustrative Table 1 includes only six patient attributes, more typically the number of patient attributes generated from content of the patient information database will be much larger; for example, in some contemplated embodiments operating on the CVIS 10, the number of attributes in the patient data table 14 is expected to be on the order of hundreds of attributes, e.g. 200 attributes in one example.

TABLE 1

An illustrative example of pre-processed CVIS patient data

| ID | Gender | PCI History | Hemoglobin | MI History | CRP | Bleeding |
|---|---|---|---|---|---|---|
| 1 | Male | Yes | Abnormal | No | Abnormal | Yes |
| 2 | Female | No | Abnormal | No | Abnormal | No |
| 3 | Male | No | Normal | Yes | Normal | No |
| 4 | Female | Yes | Normal | No | Normal | No |
| 5 | Female | Yes | Abnormal | No | Abnormal | Yes |
| 6 | Male | No | Normal | No | Normal | No |

With continuing reference to FIG. 1, the pattern discovery visual analytic techniques disclosed herein make use of a predictive model for predicting whether an attribute T of the set of attributes has a value t, that is, predicts whether T=t. The predictive model is parameterized by w attributes, so that given as input the attribute values for the w attributes the model outputs a prediction of whether T=t. In illustrative embodiments, the predictive model is a predictive pattern 20 of attribute values for the w attributes 22. The predictive pattern 20 is applied by a prediction engine 24 to generate a positive or negative prediction for the target value t of the target attribute T of the set of attributes tabulated in the patient data table 14 using the prediction pattern 20 of attribute values for the w attributes 22 of the set of attributes. The prediction for a given patient is a positive prediction (T=t) if at least a threshold fraction 26 (denoted herein as threshold fraction e) of the w attributes 22 of the patient in the patient data table have attribute values that match the prediction pattern 20; the prediction is a negative prediction (T # t) otherwise. It is contemplated to have the threshold e=1, in which case it would be required for every one of the w attribute values of the patient to match the value for that attribute in the prediction pattern 20 in order to output a positive prediction. In other embodiments, e<1 so that fewer than all of the attributes must match in order to output a positive prediction (i.e. to output prediction T=t). An example predictive pattern using w=3 attributes from Table 1 is:

PCI History=Yes AND Hemoglobin=Abnormal AND CRP=Abnormal→Bleeding=Yes

In this illustrative predictive pattern, the target attribute T is "Bleeding" and the target value is "Yes". The w=3 input attributes are "PCI History", "Hemoglobin", and "CRP" whose respective matching values are "Yes", "Abnormal", and "Abnormal". In one suitable embodiment, e=⅔ so that a patient matches this pattern if at least two of the three attribute values of the patient match the specified matching values. Missing attribute values may be handled in various ways. In one approach, any missing attribute value is assumed to not match, and the threshold e is optionally scaled by the number m of missing attribute values, i.e.

$$e \to \frac{w-m}{w}e \text{ where } (w-m)$$

is the number of available attributes.

The predictive pattern 20 can be obtained from various sources, such as from clinical studies identifying correlations between the target attribute value t and various other patient attributes, and/or from first principles analysis based on expected physiological relationships between the target attribute T and other patient attributes. As disclosed herein, the pattern discovery visual analytic device may optionally be used to adjust the predictive pattern, for example by removing less distinguishing attributes, changing the matching value for an attribute, and/or testing the addition of new attributes to the pattern.

With continuing reference to FIG. 1, the predictive pattern 20 is applied by the prediction engine 24 to produce predictions of whether T=t for the patients of the patient data table 14. Furthermore, the patient data table 14 tabulates actual values of the attribute T for the patients tabulated in the patient data table 14. Thus, sufficient information is available to generate a confusion matrix 30 as a 2×2 matrix having four patient groups (also referred to herein as four "proportions"): a true positive (TP) patient group or proportion for which the predictive pattern 20 predicts T=t and the patient actually has value t for attribute T in the patient data table 14; a true negative (TN) patient group or proportion for which the predictive pattern 20 predicts T≠t and the patient actually has an attribute value other than t for attribute T in the patient data table 14; a false positive (FP) patient group or proportion for which the predictive pattern 20 predicts T=t but the patient actually has an attribute value other than t for attribute T in the patient data table 14; and a false negative (FN) patient group or proportion for which the predictive pattern 20 predicts T≠t but the patient actually has value t for attribute T in the patient data table 14. In this grouping approach, both TP and TN proportions are correct pattern predictions on positive and negative cases respectively. On the other hand, FP and FN are incorrect pattern predictions.

As illustration, referring back to the illustrative patient data table of Table 1 and using the previous prediction pattern for T=t being "Bleeding"="Yes" with e=⅔, Table 2 shows the w=3 attributes and whether each matches for the patient, along with the resulting prediction for "Bleeding", the actual "Bleeding" attribute value tabulated in Table 1, and in the rightmost column the proportion.

TABLE 2

"Bleeding" = "Yes" predictions

| PCI ID | PCI History | Hemo-globin | CRP | Bleeding Prediction | Bleeding (Actual) | Pro-portion |
|---|---|---|---|---|---|---|
| 1 | Match | Match | Match | Yes | Yes | TP |
| 2 | No match | Match | Match | Yes | No | FP |
| 3 | No match | No match | No match | No | No | TN |
| 4 | Match | No match | No match | No | No | TN |
| 5 | Match | Match | Match | Yes | Yes | TP |
| 6 | No match | No match | No match | No | No | TN |

The illustrative pattern discovery visual analytic examples described herein operate on a proportion, such as the TP proportion. In such cases, only the proportion selected for visual analytic processing must be grouped, although the other three proportions may optionally also be grouped to facilitate switching between proportions if desired.

Figure 2:
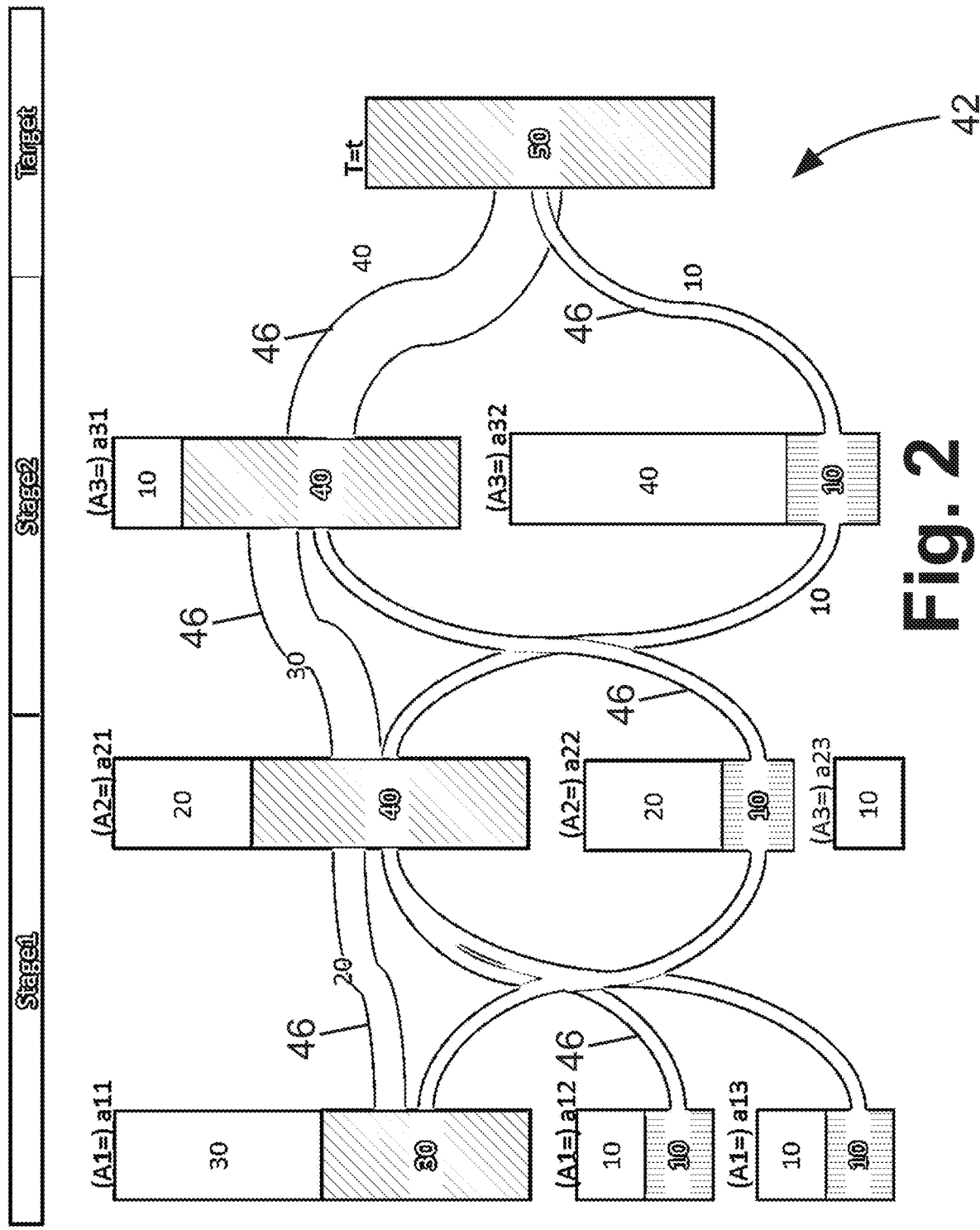
FIGS. 2-4 diagrammatically show illustrative directed graph representations of patient statistics for a selected proportion of the confusion matrix generated by the device of FIG. 1 shown on a per-attribute basis for attributes of the predictive pattern processed by the device of FIG. 1.

With continuing reference to FIG. 1 and with further reference to FIG. 2, a visual user interface 40 displays, on the display component 4 of the computer 2, a representation 42 of patient statistics for the selected proportion of the confusion matrix 30 on a per-attribute basis for attributes of the w attributes. FIG. 2 illustrates an enlarged view of the illustrative representation 42, which includes a portion of a directed graph of the w attributes of the target prediction pattern 20. In this representation 42, the w attributes are ordered in a defined sequence. In some embodiments, the defined sequence represents a time sequence of clinical stages ("Stage 1" and "Stage 2" in illustrative representation 42), with one or more attributes assigned to each clinical stage such that the attribute value for each attribute assigned to a clinical stage is generated during that clinical stage. The illustrative representation 42 is for the true positive (TP) proportion, and the directed graph terminates in the result T=t. In the directed graph, each attribute is represented by one or more attribute value nodes each representing the fraction of patients of the selected proportion of the confusion matrix 30 having the corresponding attribute value, and edges of the directed graph are represented by flow connectors each extending between two adjacent attributes in the defined sequence and connecting an attribute value node of one of the adjacent attributes with an attribute value node of the other of the adjacent attributes. Each flow connector has a width (or other graphical representation, e.g. darkness or lightness) representing the fraction of patients of the selected proportion of the confusion matrix 30 having both attribute values represented by the respective attribute value nodes connected by the flow connector.

The user input device 6, 8 may be used by a user to select a node or flow connector of the directed graph, e.g. by clicking on it using the mouse 8 to control an on-screen mouse pointer, or by tabbing between the different nodes and flow connectors using a "tab" key of the keyboard 6 and pressing the "enter" key when the desired node or flow connector is highlighted. In response to the selection, information about a patient cohort 44 is displayed. The patient cohort 44 is defined as the fraction of patients of the selected proportion of the confusion matrix 30 represented by the user-selected node or flow connector. In similar fashion, the user may select two or more nodes of the displayed directed graph, and the patient cohort 44 is then defined as the combined fractions of patients of the selected proportion of the confusion matrix 30 represented by the selected two or more nodes. If a flow connector is selected then the cohort 44 corresponding to the flow connector is the set of patients defined by the joint statistics for the adjacent attributes, e.g. the fraction of patients having both the attribute value of the attribute value node at the start of the flow connector and the attribute value of the attribute value node at the terminus of the flow connector. It will be appreciated that the patient fractions can be represented using various types of statistics, such as fractions, percentages, total counts, or so forth.

With continuing reference to FIG. 2, some illustrative directed graph visualizations are described. On a certain prediction proportion of the confusion matrix 30, the patient flow is the time (stage) oriented patient attribute-value path according to the discovered pattern. The attributes are pre-defined or configured such that they belong to various time-order stages according to the clinical analysis task. For example, the clinical workflow of a PCI patient can be split into six stages including pre-procedure and post-procedure stages. For other diseases, the clinical workflow will be different from the example here. The pattern discovery visual analytics device provides an attributes editing tool (not shown) via which a user can edit the number/ordering of clinical stages for a specific clinical task and assign patient attributes to the clinical stages. To generate the patient flows, all unique attribute-value combinations falling into the proportion selected for visualization are computed, and the corresponding records are grouped and arranged in a way that the user can select any connections between two time-ordered attributes to generate the patient cohort 44 including the patients within.

The following notation is used. The prediction target is T=t where T is the target attribute and t is the target attribute value. A time order sequence of clinical stages S={$s_1$, $s_2$, . . . , $s_k$} is defined, where k is the number of clinical stages. Each clinical stage has one or more attributes assigned to it, with all w attributes 22 of the predictive pattern 20 being assigned to clinical stages. The w attributes are denoted where this is an ordered sequence. The attribute values for a node $A_i$ are denoted as $a_{i1}$, $a_{i2}$, and so forth. A binary attribute has only two allowable values, i.e. a binary attribute $A_i$ can only assume a first value denoted $a_{i1}$ or a second value denoted $a_{i2}$.

In FIG. 2, the following notation is used. For the attribute value node representing the value $a_{11}$ of attribute $A_1$ the attribute value node is labeled (A1=)a11. The attribute value node representing the value $a_{12}$ of attribute $A_1$ is labeled (A1=)a12. The attribute value node representing the value $a_{13}$ of attribute $A_1$ is labeled (A1=)a13. The attribute value node representing the value $a_{21}$ of attribute $A_2$ is labeled (A2=)a21. The attribute value node representing the value $a_{22}$ of attribute $A_2$ is labeled (A2=)a22. The (empty) attribute value node representing the value $a_{23}$ (which is not represented by any patients of the selected proportion) of attribute $A_2$ is labeled (A2=)a23. The attribute value node representing the value $a_{31}$ of attribute $A_3$ is labeled (A3=)a31. Finally, the attribute value node representing the value $a_{32}$ of attribute $A_3$ is labeled (A3=)a32. In FIG. 2 the flow connectors are labeled as flow connectors 46 (not all flow connectors are so-labeled in order to avoid excessive cluttering of the drawing).

If a clinical stage has two or more attributes assigned to it, the ordering of those attributes within the stage can be arbitrarily chosen to produce the defined order. This reflects the usual situation in which laboratory tests or other activities generating patient attributes are typically scheduled within a clinical stage without a particular ordering, e.g. based on availability of the required equipment and personnel. In the directed graph, the flow is from the earlier clinical stages to the later clinical stages and, in illustrative FIG. 2, terminates at a terminal node representing the prediction T=t. Since FIG. 2 represents the true positives proportion for which the predictive pattern 20 predicts T=t, all patients belong to this final node T=t in this illustrative example. Each attribute value node stores a statistic (i.e. patient fraction) of patients of the selected proportion having the corresponding attribute value for that attribute. In the case of a binary attribute, there are exactly two attribute value nodes, e.g. for a laboratory test result attribute $A_i$ having possible values "normal" or "abnormal" there is one attribute value node for $A_i$=Normal and a another attribute node for $A_i$=Abnormal.

In some embodiments the attribute value nodes of the directed graph are color-coded as to whether the corresponding attribute value matches the prediction pattern. In illustrative FIG. 2, this is diagrammatically indicated by using slanted shading (e.g. corresponding to green) to indicate attribute value nodes corresponding to attribute values that match the predictive pattern 20 and using vertical shading (e.g. corresponding to red) to indicate attribute value nodes corresponding to attribute values that do not match the predictive pattern 20. Missing attribute values are diagrammatically shown without shading, which may for example represent grayed out coloring. In the illustrative directed graph of FIG. 2, a node without any flow (A3=a23) is shown without shading, but alternatively may be omitted entirely. Percentage values can be optionally displayed/hidden as well.

Patient fractions corresponding to a flow connector are the cohort of patients with both attribute values at the beginning and end of the flow connector. The patient fraction can be shown along with the edge when hovering, and become clickable for the user to retrieve the corresponding patient cohort. The flow connectors can be colored using the same colors as those of the starting and ending attribute value nodes, with suitable color shading or color transition when the two connected attribute value nodes are of different colors.

In this approach, the user can identify special flows with meaningful characteristics for clinical study or follow-up to improve quality of care. The user can click on any flow connector to investigate the corresponding patients.

In another embodiment, users can also select multiple attribute value nodes and then the patient cohort can be generated according for retrieval. The cohort for two selected attribute value nodes is the set of patients having both attribute values for the respective attributes. More generally, the cohort for two or more selected attribute value nodes is the intersection of the fractions of patients belonging to all selected nodes. (Note that if two attribute value nodes for the same attribute are selected then the cohort is the empty set since a patient always has a single attribute value for a given attribute).

In the illustrative example of FIG. 2 and considering Table 1 with A1=PCI History, A2=CRP, and A3=Hemoglobin, the "Stage 1" clinical stage has two assigned attributes: PCI History and CRP, while the "Stage 2" clinical stage has one assigned attribute: Hemoglobin. In this example, patients flow according to the following paths: Stage 1→Stage 2→Target (Bleeding). The time-ordered attributes are PCI History/CRP/Hemoglobin. There is no basis for distinguishing attribute orders within the same clinical stage (e.g., attributes PCI History and CRP both in Stage 1 in this example), so an arbitrary ordering PCI→CRP is chosen within stage 1. With this time order, a patient flow can be generated.

For the illustrative six patient of Table 1, In the TP proportion (Pattern matched=positive, actual Bleeding=Yes), there is only 1 unique combination according to the data: Yes/Abnormal/Abnormal for PCI History/CRP/Hemoglobin, with patients ID=1 and ID=5. These two patients flow through PCI History=Yes, CRP=Abnormal, and then Hemoglobin to the end-point target Bleeding=Yes.

On the other hand, in the TN proportion (Pattern NOT matched=negative, actual Bleeding=No), there are 2 paths: No/Normal/Normal (IDs 3, 6) and Yes/Normal/Normal (ID 4). These paths are used to generate the graph (or the illustrated embodiments) such that users can easily select patients for example from PCI History=No→CRP=Normal in stage 1 with target Bleeding=No.

Summarizing all paths of the full pattern, there can be a patient population view of all full-length cohorts available for comprehensive cohort study purposes. For each unique path of a particular attribute-value combination with all attributes in the pattern, a cohort of patients is generated, their statistics such as number of cases, matching percentage, and specific mismatched attribute-values are shown to enable user to analyze the characteristics (along the time line of stages) for cohort selection. The user can select on such a cohort and link to the patient information database 10 to take further actions. In another embodiment, the user can also select multiple full cohorts.

Figure 3:
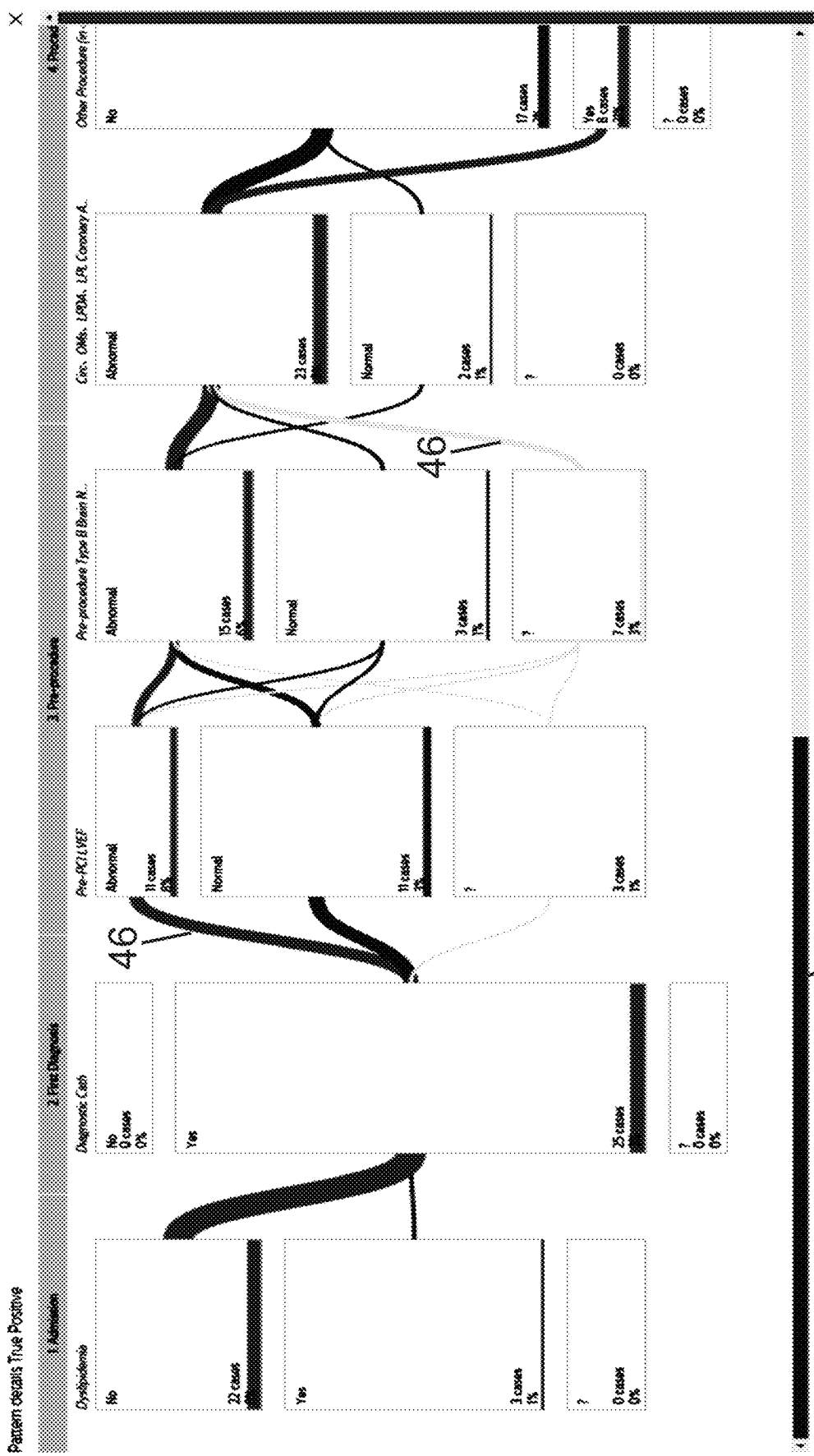
Figure 4:
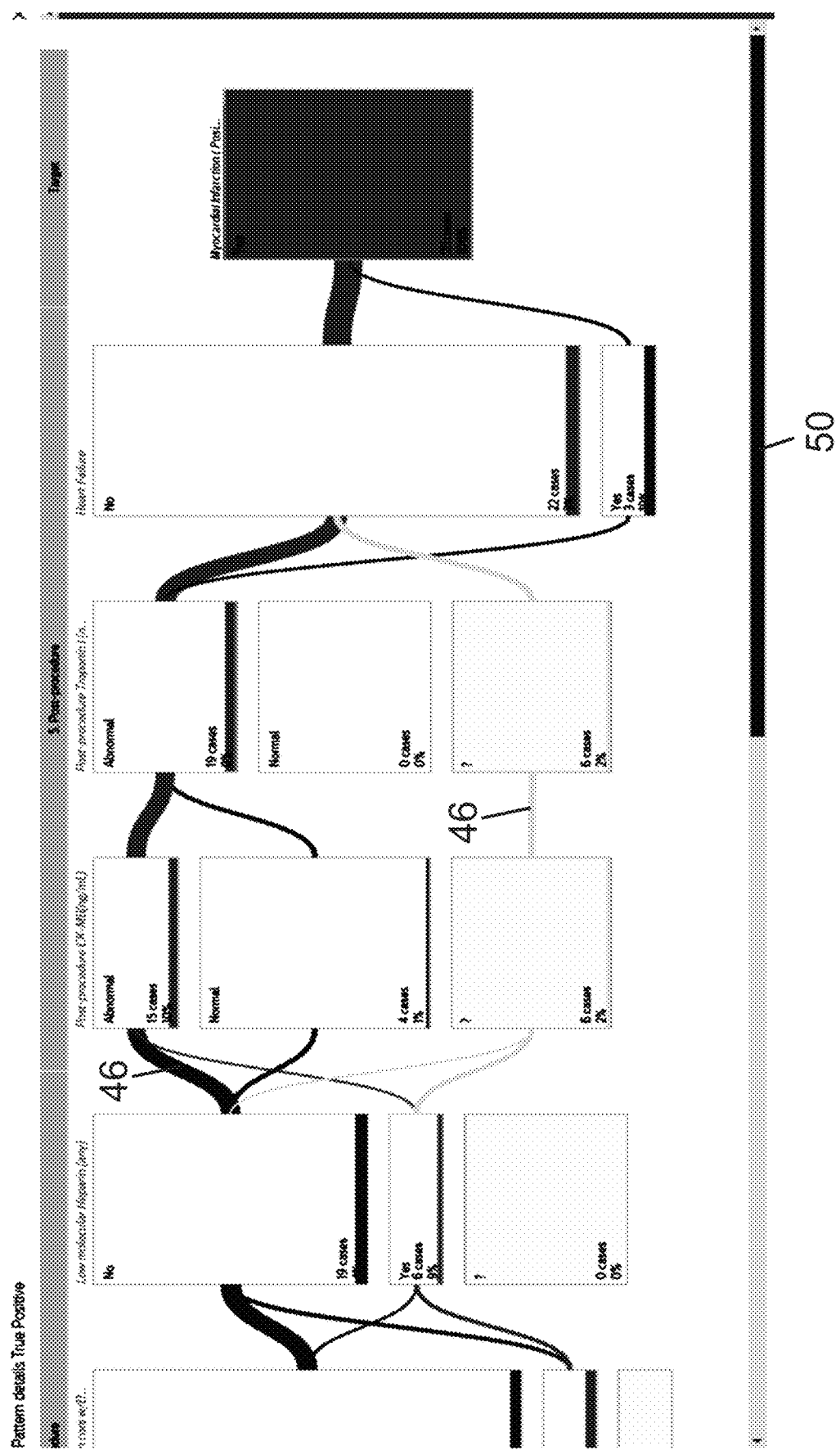

With reference to FIGS. 3 and 4, and again using the configuration for the PCI task, all attributes and categories are mapped to a non-overlapping sequential ordered set of clinical stages. In the patient flow, the attributes are grouped according to the stage order, e.g. stage 1=Admission; stage 2=First Diagnosis, and so forth. Attributes in the same stage, thus without order information, are ordered arbitrarily. According to the selected proportion of the confusion matrix 30, how the patients go through different stages to the end point, and to the prediction target value, are illustrated by the directed graph of FIGS. 3 and 4 (where FIG. 3 shows a leftmost portion of the directed graph and FIG. 4 shows the rightmost portion of the directed graph, the sliding being accomplished using a horizontal scroll bar 50).

Each column of the directed graph represents an attribute, with the attribute value nodes of the attribute stacked vertically. The attribute nodes are shown in this example as boxes sized according to their patient fractions in the proportion. Boxes at the bottom labeled with "?" show the proportions of missing values of the attributes. Although not shown, the boxes (attribute value nodes) may be color coded according to whether the attribute value matches the predictive pattern 20. For example, matching attribute values may be colored green, while non-matching attribute values may be colored red. The optional nodes representing patients for which the attribute is missing (that is, the particular patient has no value for the attribute) are colored, e.g. in grey. In this color scheme, flow connectors going from one box (attribute value node) to another following the stage order are colored as follows: match→match: green; mismatch→mismatch: red; mismatch→match: red transitioning to green; or match→mismatch: green transitioning to red. Any flow connector running to or from a box with "?" (missing) is either omitted or colored grey. Again, this is merely an illustrative color scheme, and other color schemes may be employed, and/or other graphical coding may be employed such as different types of hatching or shading.

In the displayed directed graph, patient counts and information associated with a particular attribute value node or flow connector may be brought up in a pop-up window or the like by hovering the mouse pointer over the node or flow connector and/or by clicking on the node or flow connector using the illustrative mouse 8, or a touchscreen or other user input device. This information is for the cohort represented by the node or flow connector. More specific patient information for patients of the cohort may be retrieved from the patient data table 14 or from the CVIS 10 itself.

It is also contemplated to provide additional analytics views such as a table view of all patients of a proportion of the confusion matrix 30, with table rows corresponding to patients, table columns corresponding to attributes, and table cells containing the attribute values for the patient/attribute table coordinates with the table cells color coded as just described to indicate whether each attribute value matches the predictive pattern 20. In such a view, patients with identical attribute values may be combined into a single table row labeled "Cohort" which can be mouse-clicked or otherwise selected to expand the "Cohort" column to display the list of patients belonging to the cohort.

Figure 5:
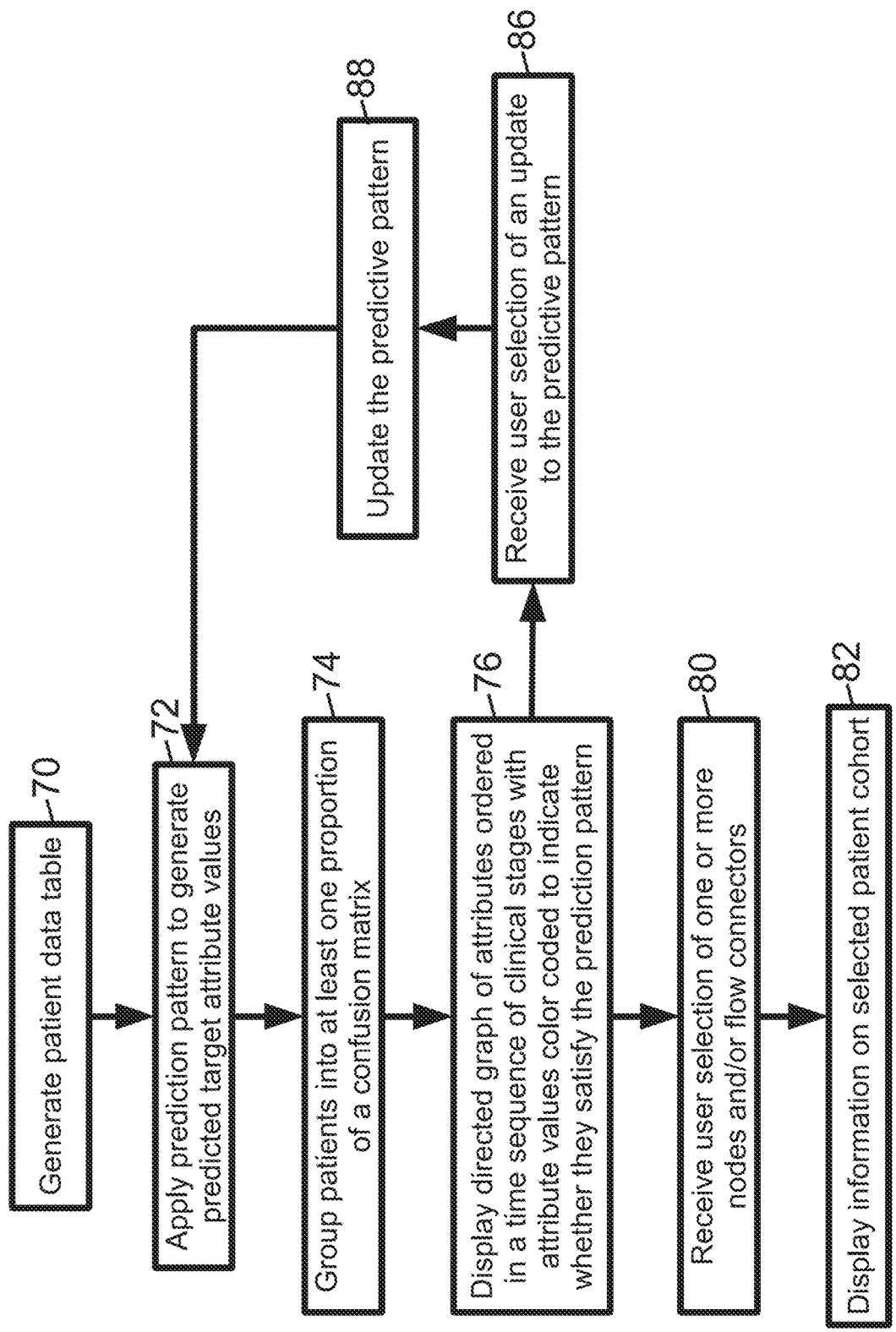
FIG. 5 diagrammatically shows a pattern discovery analytics method suitably performed using the device of FIG. 1.

With reference to FIG. 5, an illustrative pattern discovery visual analytics method suitably performed using the pattern discovery visual analytics device of FIG. 1 is described. In an operation 70, the patient attributes synthesizer 12 generates the patient data table 14, e.g. by converting laboratory results to binary normal/abnormal values or other data pre-processing. The operation 70 may, for example, be performed by suitable data mining algorithms that extract relevant patient attributes from the CVIS 10. The detailed pre-processing depends upon how the source patient information is stored in the CVIS 10 and upon the choice of attribute values. As previously noted, in some embodiments all attributes are converted to binary attributes which has advantages including reducing the number of attribute value nodes per attribute in the directed graph down to two (or three if a missing value node is shown). Such conversion can also produce attribute values that are readily interpreted by the clinician (e.g., "normal" or "abnormal" is more readily interpreted than some quantitative test result value) and simplifies the computational implementation of the prediction pattern 20. However, it is also contemplated for an attribute to be capable of assuming one of three or more (non-missing) values. An example of a non-binary attribute is attribute $A_1$ of FIG. 2 which can assume values of the set $\{a_{11}, a_{12}, a_{13}\}$; whereas each of the attributes $A_2$ and $A_3$ of that example are binary attributes.

In an operation 72, the prediction engine 24 is applied to generate predicted target attribute values for patients of the patient data table 14. In an operation 74 the patients are grouped into at least one selected proportion of the confusion matrix 30. In an operation 76, the directed graph 42 of the w attributes parameterizing the prediction pattern 20 is displayed on the display component 4 of the computer 2, ordered in a time sequence of clinical stages, optionally with attribute values color coded to indicate whether they satisfy the prediction pattern. In an operation 80, a user selection of one or more nodes and/or flow connectors is received via the user input device 6, 8. In an operation 82, information on the cohort defined by the selected node(s) and/or flow connector(s) is displayed, and optionally other operations are performed on the cohort such as providing a list of patients belonging to the cohort. If two or more nodes are selected, then the cohort is suitably the intersection of the patient fractions of the selected nodes since the intersection contains those patients having all of the attribute values corresponding to the selected attribute value nodes. The cohort defined by a flow connector is the intersection of the patient fractions of the two attribute value nodes connected by the flow connector.

The directed graph 42 can also be used to perform other analytic operations. For example, it can be used to investigate possible adjustments to the target prediction pattern 20. As an illustration, in an operation 86 the user selects an update to the predictive pattern 20. As one example, consider a directed graph displaying the true positive proportion. If the user notices that a large fraction of patients have a value for an attribute $A_n$ that does not match the pattern, this may indicate that the attribute is not very predictive of T=t. In this case, the user may elect to select the attribute $A_n$ in the operation 86 along with an instruction to remove the attribute $A_n$ from the predictive pattern 20. In response, the computer 2 removes the attribute $A_n$ from the predictive pattern to produce an updated (and simplified) predictive pattern 20, and flow returns to operation 72 to regenerate the directed graph without the attribute $A_n$. The user can then review the resulting directed graph to assess the impact of removal of $A_n$ on the predictive performance.

Such removal of attributes can be particularly valuable in the case of tasks that require evaluation at an early stage of treatment. For example, in attempting to generate a patient cohort for comparison with a current clinical patient, it would be useful to remove as many nodes as practicable from the later clinical stages that the current clinical patient has not yet reached. In this way, the user can identify the most critical attributes in these later stages in order to better focus the clinical patient's subsequent treatment based on analysis of the comparative cohort.

Likewise, the user can add attributes to the predictive pattern (thereby increasing w), or change the matching value for an attribute in the predictive pattern, or so forth, and use the device of FIG. 1 to interactively view the impact of these changes on performance of the predictive pattern. Another adjustment that can be interactively investigated is adjustment of the matching threshold e. In general, increasing e will reduce the number of patients that match the predictive pattern 20, while decreasing e will increase the number of matching patients.

With returning reference to FIG. 1, the various computational blocks 12, 24, 40 may be implemented by suitable programming of the computer 2. Further, the disclosed pattern discovery visual analytics techniques may be embodied by a non-transitory storage medium storing instructions executable by an electronic processor (e.g. the computer 2) to perform the disclosed analytics. The non-transitory storage medium may, by way of non-limiting example, include a magnetic disk or other magnetic storage medium, an optical disk or other optical storage medium, a solid state drive, flash drive or other electronic storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A pattern discovery visual analytics device comprising:
a patient information database;
a computer including a display component, the computer programmed to perform a method including:
generating a patient data table from patient information contained in the patient information database that tabulates, for each patient of the patient data table, attribute values for a set of attributes;
for each patient of the patient data table, generating a positive or negative prediction for a target value t of a target attribute T of the set of attributes using a prediction pattern of attribute values for w attributes of the set of attributes, the prediction for a patient being a positive prediction if at least a threshold fraction e of the w attributes of the patient in the patient data table match the prediction pattern and being a negative prediction otherwise;
grouping each patient of the patient data table into a confusion matrix that includes true positive, false positive, true negative, and false negative proportions in accord with the positive or negative predictions for the target value t of the target attribute T and actual values of the target attribute T in the patient data table;
generating a patient cohort based on one or more selected proportions of the confusion matrix, wherein any of the four proportions of the confusion matrix may be selected to generate the patient cohort; and
displaying, on the display component of the computer, a representation of patient statistics or attribute value statistics for the generated patient cohort on a per-attribute basis for attributes of the w attributes.

2. The pattern discovery visual analytics device of claim 1 wherein the displaying includes:
displaying at least a portion of a directed graph of the w attributes in which:
(i) the w attributes are ordered in a defined sequence and
(ii) each attribute is represented by one or more attribute value nodes each representing the fraction of patients of the selected proportion of the confusion matrix having the corresponding attribute value and
(iii) edges of the directed graph comprise flow connectors each extending between two adjacent attributes in the defined sequence and connecting an attribute value node of one of the adjacent attributes with an attribute value node of the other of the adjacent attributes.

3. The pattern discovery visual analytics device of claim 2 wherein each flow connector has a width representing the fraction of patients of the selected proportion of the confusion matrix having both attribute values represented by the respective attribute value nodes connected by the flow connector.

4. The pattern discovery visual analytics device of claim 2 wherein the defined sequence of the w attributes represents a time sequence of clinical stages wherein one or more attributes are assigned to each clinical stage and the attribute value for each attribute assigned to a clinical stage is generated during that clinical stage.

5. The pattern discovery visual analytics device of claim 2 wherein the computer further comprises:
at least one user input device capable of selecting a node or flow connector of the directed graph;
wherein the method further includes responding to selection via the at least one user input device of a node or flow connector of the directed graph by displaying information about the generated patient cohort defined as the fraction of patients of the selected proportion of the confusion matrix represented by the selected node or flow connector.

6. The pattern discovery visual analytics device of claim 5 wherein the at least one user input device is capable of selecting two or more nodes of the directed graph and the method further includes responding to selection via the at least one user input device of two or more nodes of the directed graph by displaying information about the intersection of the generated patient cohort represented by the selected two or more nodes.

7. The pattern discovery visual analytics device of claim 2 wherein the attribute value nodes of the directed graph are color-coded as to whether the corresponding attribute value matches the prediction pattern.

8. The pattern discovery visual analytics device of claim 7 wherein the flow connectors of the directed graph are color-coded at each end to match with the color coding of the attribute value node connected at that end.

9. The pattern discovery visual analytics device of claim 2 wherein, in the directed graph, at least one attribute is represented by a further attribute node representing the fraction of patients of the selected proportion of the confusion matrix having no attribute value in the patient data table for the corresponding attribute.

10. The pattern discovery visual analytics device of claim 2 wherein the selected proportion of the confusion matrix is one of the true positive proportion and the true negative proportion, and the directed graph further includes a terminal node representing the attribute value t of the target attribute T placed at the end of the defined sequence in the directed graph.

11. The pattern discovery visual analytics device of claim 1 wherein the displaying includes:
   displaying, for each displayed attribute of the w attributes, a representation of attribute value statistics for the attribute in the selected proportion of the confusion matrix;
   displaying the representations of attribute value statistics for the displayed attributes of the w attributes ordered in a defined sequence of the w attributes; and
   displaying flow connectors between adjacent attributes of the defined sequence wherein each flow connector represents joint statistics for the adjacent attributes.

12. The pattern discovery visual analytics device of claim 11 wherein:
   the representation of attribute value statistics for each displayed attribute comprises a node for each attribute value of the displayed attribute representing a statistic of patients of the selected proportion of the confusion matrix having that attribute value; and
   each flow connector connects nodes of the respective adjacent attributes and represents a statistic of patients of the selected proportion of the confusion matrix having both attribute values represented by the respective nodes connected by the flow connector.

13. The pattern discovery visual analytics device of claim 12 wherein the defined sequence of the w attributes represents a time sequence of clinical stages wherein the one or more attributes assigned to each clinical stage are generated during that clinical.

14. The pattern discovery visual analytics device of claim 1 wherein the generating of the patient data table includes generating the attribute values as binary values such that each attribute of the set of attributes has exactly two allowable values;
   wherein values of each attribute representing a clinical test are tabulated in the patient data table as binary values indicating either a normal test result or an abnormal test result for the clinical test.

15. A computer-implemented pattern discovery visual analytics method comprising:
   for each patient of a population, generating a positive or negative prediction for a target value t of a target attribute T using a computer that is programmed to compare a prediction pattern for w attributes to corresponding attribute values of the patient;
   using the computer, grouping patients of the population into a confusion matrix that includes true positive, false positive, true negative, and false negative proportions in accord with the positive or negative predictions for the target value t of the target attribute T and actual values of the target attribute T for the patients;
   using the computer, generating a patient cohort based on one or more selected proportions of the confusion matrix, wherein any of the four proportions of the confusion matrix may be selected to generate the patient cohort; and
   displaying, on a display component of the computer, a representation of patient statistics or attribute value statistics for the generated patient cohort with attributes of the w attributes represented by attribute value nodes each representing the fraction of patients of the selected proportion having the corresponding attribute value.

* * * * *